(12) United States Patent
Thompson et al.

(10) Patent No.: US 8,034,838 B2
(45) Date of Patent: Oct. 11, 2011

(54) COMPOSITION AND METHOD FOR THE TREATMENT OF NEUROLOGICAL DISORDERS

(76) Inventors: Daryl Lee Thompson, Winter Haven, FL (US); Milton Joseph Ahrens, Lake Alfred, FL (US)

( * ) Notice: Subject to any disclaimer, the term of this patent is extended or adjusted under 35 U.S.C. 154(b) by 196 days.

(21) Appl. No.: 12/474,740

(22) Filed: May 29, 2009

(65) Prior Publication Data

US 2009/0298932 A1    Dec. 3, 2009

Related U.S. Application Data

(60) Provisional application No. 61/056,962, filed on May 29, 2008.

(51) Int. Cl.
*A61K 31/352* (2006.01)

(52) U.S. Cl. ....................................... 514/456; 514/455

(58) Field of Classification Search .................. 514/455, 514/456
See application file for complete search history.

(56) References Cited

U.S. PATENT DOCUMENTS

| | | |
|---|---|---|
| 2006/0137207 A1 | 6/2006 | Caldwell et al. |
| 2007/0116779 A1 | 5/2007 | Mazzio |
| 2008/0021096 A1 | 1/2008 | Maher |
| 2008/0044390 A1 | 2/2008 | Jin et al. |
| 2008/0292607 A1 | 11/2008 | Mazzio et al. |
| 2009/0130051 A1 | 5/2009 | Jarrott et al. |

*Primary Examiner* — Jennifer M Kim
(74) *Attorney, Agent, or Firm* — Renner, Otto, Boisselle & Sklar, LLP

(57) ABSTRACT

The composition for treating neurological disorders such as Alzheimer's Disease is provided. The composition includes a modified flavonoid compound having enhanced binding affinity to metabolic modulating enzymes. The composition is effective to down-regulate beta- and gamma-secretase and up-regulate alpha secretase, which results in a reduction in amyloid proteins.

3 Claims, No Drawings

COMPOSITION AND METHOD FOR THE TREATMENT OF NEUROLOGICAL DISORDERS

This application claims the benefit of U.S. Provisional Application No. 61/056,962, filed on May 29, 2008, which is incorporated herein in its entirety.

BACKGROUND

In general, the present invention is related to the treatment, prevention and amelioration of neurological disorders, e.g., Alzheimer's disease, and symptoms thereof.

Alzheimer's disease is an irreversible, progressive brain disease and is the most common cause of dementia afflicting 30 million people worldwide. With Alzheimer's disease, parts of the brain essential for cognitive functioning such as memory, reasoning, attention, language, and behavior degenerate to such an extent that it interferes with a person's daily life and activities.

Although the cause of Alzheimer's disease is not fully understood, it is known that damage to the brain begins as many as 10 to 20 years before the symptoms are evident. Alzheimer's disease is characterized by the deposition of "plaques", aggregates of β-amyloid peptide fragments, on brain cells, interfering with cognitive function. In addition, Alzheimer's disease is characterized by the presence of numerous neurofibrillary "tangles", consisting of paired helical filaments which abnormally accumulate in the neuronal cytoplasm. Recent studies suggest that providing a drug to reduce, eliminate or prevent β-amyloid peptide formation, deposition and/or accumulation in the brains of patients will provide an effective therapeutic.

Currently there is no cure for Alzheimer's disease. However, drug and non-drug treatments are available that may help with cognitive and behavior symptoms of Alzheimer's. Two types of drugs are currently approved by the U.S. Food and Drug Administration (FDA) to treat cognitive symptoms. The first type is cholinesterase inhibitors that are designed to prevent the breakdown of acetylcholine. These drugs delay worsening symptoms for six to twelve months for about half of the people who take them. The second type of drug works by acting on the glutamatergic system by blocking NMDA glutamate receptors. Memantine is the only currently available drug of this type.

There is a need to develop and identify new compounds or agents as potential therapeutic agents for treating, preventing, or ameliorating Alzheimer's disease and other neurological disorders, such as Parkinson's disease and Huntington's disease.

SUMMARY

In one aspect of the invention, there is provided a composition for treating neurological diseases. The composition includes a modified flavonoid compound having at least one binding affinity enhancer. The binding enhancer is an electrophilic group that increases the enzyme affinity of the compound.

In another aspect of the invention there is provided a method of treating a neurological disorder in a subject including administering to the subject an effective amount of a modified flavonoid compound wherein the flavonoid compound has been modified by the addition of at least one binding affinity enhancer to effect a down regulation of beta- and gamma-secretase and an up regulation of alpha secretase effecting a reduction in amyloid proteins.

In one embodiment, a composition for treating or preventing Alzheimer's disease or neurological disease is provided. The composition includes a therapeutically effective amount of a modified flavonoid compound of the general formula:

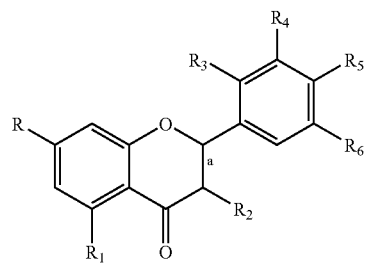

wherein R, $R_1$, $R_2$, $R_3$, $R_4$, $R_5$ and $R_6$ are each independently hydrogen, a hydroxy group, an alkoxy group, a rutinosyl group, and a rhamnosyl group; and a is a single bond or a double bond; provided that at least one of R, $R_1$, $R_2$, $R_3$, $R_4$, $R_5$ and $R_6$ comprises an electrophilic group chosen from aldehyde, haloalkane, alkene, butyryl, fluorophenol, sulfonamide and fluorophenyl sulfoxide.

In one embodiment, at least one of R and $R_5$ of the composition includes an electrophilic group.

In another embodiment, $R_1$=OH, $R_2$=OH, $R_3$=H, $R_4$=OH and $R_6$=OH; and at least one of $R_5$ and R includes an electrophilic group.

In yet another embodiment, the electrophilic group is chosen from butyryl, sulfonamide, fluorophenol and fluorophenyl sulfoxide.

In one embodiment, the modified flavonoid includes a compound having the structure:

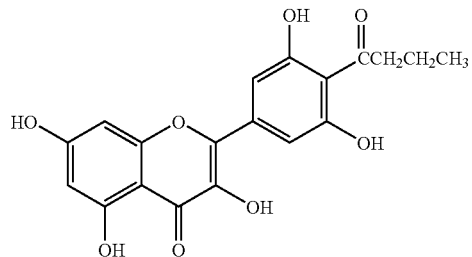

In another aspect of the invention there is provided a pharmaceutical composition including a pharmaceutically acceptable carrier in combination with a composition having the structure:

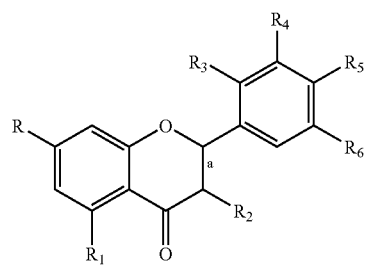

wherein R, $R_1$, $R_2$, $R_3$, $R_4$, $R_5$ and $R_6$ are each independently hydrogen, a hydroxy group, an alkoxy group, a rutinosyl group, and a rhamnosyl group; and a is a single bond or a double bond; provided that at least one of R, $R_1$, $R_2$, $R_3$, $R_4$, $R_5$ and $R_6$ comprises an electrophilic group chosen from aldehyde, haloalkane, alkene, butyryl, fluorophenol, sulfonamide and fluorophenyl sulfoxide.

In yet another aspect of the invention, there is provided a method of making a compound for treating or preventing Alzheimer's disease or neurological disorder including the steps of: providing a naturally occurring flavonoid compound having the structure:

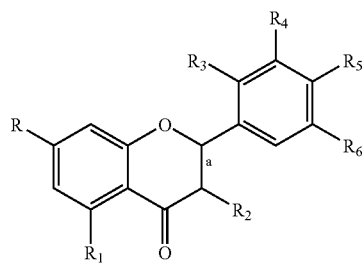

wherein R, $R_1$, $R_2$, $R_3$, $R_4$, $R_5$ and $R_6$ are each independently hydrogen, a hydroxy group, an alkoxy group, a rutinosyl group, and a rhamnosyl group; and a is a single bond or a double bond; and substituting at least one of R, $R_4$, $R_5$ and $R_6$ with an electrophilic group chosen from aldehyde, haloalkane, alkene, butyryl, fluorophenol, sulfonamide and fluorophenyl sulfoxide.

DETAILED DESCRIPTION

"Treating" a condition or disease refers to curing as well as preventing, inhibiting, reducing, and/or ameliorating at least one symptom of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

The present invention provides novel compounds that are useful for treating neurological disorders such as Alzheimer's disease. The novel compounds include flavonoid compounds having enhanced binding affinity to metabolic modulating enzymes. The compounds may be derived from naturally occurring flavonoids and include at least one electrophilic reactive group.

Beta-amyloid peptide fragments characteristic of Alzheimer's disease are produced from longer amyloid precursor proteins (normally embedded in brain cell membranes) by the action of β- and γ-secretase. The production of β-amyloid peptide fragments is mediated by α-secretase, which interferes with the β- and γ-secretase substrate.

Sucrose intake is associated with multi-fold increases of β-amyloid peptide fragment deposition. Therefore, historical increases in the intake of refined sugar and consequent disruption of normal glucose metabolism may have resulted in concurrent historical increases in the incidence of Alzheimer's Disease.

An effective treatment for Alzheimer's Disease includes the administration of a safe agent that would down-regulate β- and γ-secretase while concurrently up-regulating α-secretase.

There are several naturally occurring compounds that have an effect on glucose metabolism to some degree. Flavonoids have the following basic structure, wherein the bond between 2-3 may be a single or double bond:

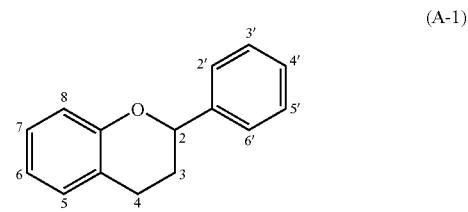

(A-1)

Two of the categories of flavonoids include flavanones and flavones. Flavanones have the structure (I) shown below and flavones have the similar structure (II) shown below:

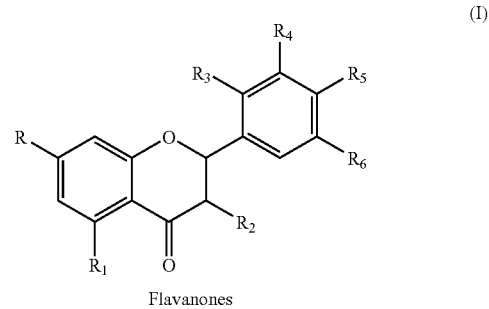

Flavanones (I)

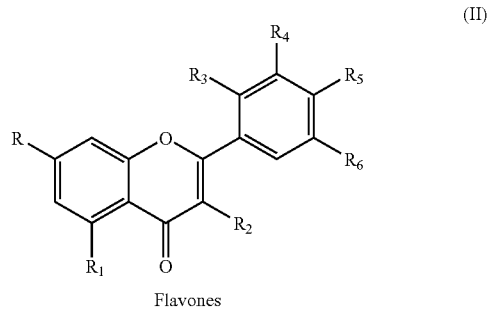

Flavones (II)

wherein R, $R_1$, $R_2$, $R_3$, $R_4$, $R_5$ and $R_6$ are each independently hydrogen, a hydroxy group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. Several examples of the bioflavonoids of formula (I) and (II) are shown below in Table 1.

TABLE 1

| | R | $R_1$ | $R_2$ | $R_3$ | $R_4$ | $R_5$ | $R_6$ |
|---|---|---|---|---|---|---|---|
| FLAVONE | | | | | | | |
| Flavone | H | H | H | H | H | H | H |
| Chrysin | OH | OH | H | H | H | H | H |
| Apigenin | OH | OH | H | H | H | OH | H |
| Luteolin | OH | OH | H | H | H | OH | H |
| Diosmin | —O-rutinose | OH | H | H | OH | $OCH_3$ | H |
| Fisetin | OH | H | OH | H | OH | OH | H |
| Kaempferol | OH | OH | OH | H | H | OH | H |
| Morin | OH | OH | OH | OH | H | OH | H |
| Quercetin | OH | OH | OH | H | OH | OH | H |
| Myricetin | OH | OH | OH | H | OH | OH | OH |
| Rutin | OH | OH | —O-rutinose | H | OH | OH | H |
| Rhoifolin | R-G-$^a$ | OH | H | H | H | OH | H |
| FLAVANONE | | | | | | | |
| Galangin | OH | OH | OH | H | H | H | H |
| Hesperetin | OH | OH | H | H | OH | $OCH_3$ | H |
| Eriodictyol | OH | OH | H | H | OH | OH | H |
| Naringenin | OH | OH | H | H | H | OH | H |
| Naringin | R-G-$^a$ | OH | H | H | H | OH | H |
| Neohesperidin | R-G-$^b$ | OH | H | H | OH | $OCH_3$ | H |
| Hesperidin | R-G-$^b$ | OH | H | H | OH | $OCH_3$ | H |
| Narirutin | R-G-$^b$ | OH | H | H | H | OH | H |
| Prunin | Glucose- | OH | H | H | H | OH | H |

$^a$rhamnose-glucose, L-rhamnose is linked α 1→2 to D-glucose
$^b$rhamnose-glucose, L-rhamnose is linked α 1→6 to D-glucose In one embodiment, there is provided a method of producing a drug to treat Alzheimer's Disease by enhancing the binding affinity of a flavonoid compound to metabolic modulating enzymes through the addition of at least one electrophilic reactive group. The electrophilic group is chosen from aldehydes, haloalkanes, alkenes, butyryl, fluorophenols, sulfonomides, fluorophenyl sulfoxides and hydronapthalenes. The enhanced binding affinity of the modified compound enables enhanced docking that will result in increases downregulation of HMG-COA, Acetyl CoA, β-secretase, and γ-secretase over the natural flavanoid compound. The downregulation of HMG-COA, Acetyl CoA, β-secretase, and γ-secretase causes a reduction in the production of Beta Amylase. Inhibiting beta-amyloid production results in the reduction of neural fibrils.

In one embodiment, the flavonoid that is modified to produce the compound having enhances binding affinity is myricetin. Myricetin is a bioflavonoid found in most berries, including cherry, cranberry and bilberry, and other plants, including parsley and rutabagas.

There are several methods by which flavonoids such as myricetin may be harvested from their original botanical sources. In one method, for example, extraction from botanical sources begins with a suitable seed material such as grape seeds or tomato seeds, pine bark or citrus rinds. The source material is macerated and flushed with water to separate the water soluble bioflavonoids from the bulkier pectins and fibers of the source material. This pulp wash is then treated with appropriate acids and bases as known in the art to cause precipitation. The precipitate is then washed again, dried and then concentrated to yield a fairly pure bioflavonoid composition. This composition may be further clarified to yield fractions containing the desired bioflavonoid product.

In another method, reverse osmosis may be used to remove the target bioflavonoid by filtering it out of juice streams from beverage manufacturing processes. The process of manufacturing fruit juices such as citrus, liberates the bioflavonoids from the rind and suspends them in the juice product. It is often desirable to remove these water soluble bioflavonoids because of their tendency to produce bitter or off flavors in the juice product. For example, during the manufacture of grapefruit juice, the primary grapefruit bioflavonoid naringin is released into the juice stream. Because naringin has a very distinct bitter taste, it is necessary to remove it from the product stream via the use of resin coated reverse osmosis devices to restore the proper flavor profile of the grapefruit juice. The resultant bioflavonoid is finally collected and dried to yield a fairly pure product.

Flavonoids may also be manufactured by synthetic methods. Such methods may include an Allan-Robinson Reaction which is a chemical reaction of o-hydroxylaryl ketones with aromatic anhydrides to form flavanones. Another example is Auwers Synthesis, which is a procedure that requires an acid catalyzed aldol condensation between benzaldehyde and a 3-oxypentanon to an o-hydroxychalcone. Further bromination of the alkene group gives a dibromo-adduct that rearranges to a flavanol by reaction with potassium hydroxide. A further example is a Baker-Venkataraman Rearrangement, which involves the reaction of 2-acetoxyacetophenones with base to form 1,3-diketones. The rearrangement reaction proceeds via enolate formation followed by an acyl transfer to form flavanones. An Algar-Flynn-Oyamada Reaction may also be used. In this reaction, a chalcone undergoes an oxidative cyclization to form a flavanol.

Flavonoid compounds, such as myricetin, modified by the addition of fluorine and/or sulfonyl, butyryl, or a combination of hydrophilic docking enhancers, may be used as a treatment for neurologically derived metabolic disorders such as Alzheimer's disease, Parkinson's disease, Huntington's disease or Down Syndrome.

Myricetin, a naturally occurring anti-oxidant with an excellent safety profile, is effective in regulating glucose metabolism, but due to modern food processing and refinement, is left out of current diets. Not surprisingly, due to the historical connection between glucose metabolism and Alzheimer's disease, it has been found that myricetin up-regulates α-secretase and down-regulates both β- and γ-secretase. Furthermore, myricetin has been shown to cross the blood brain barrier within 30 minutes of administration. Through the addition of docking enhancers to increase the efficacy (by increasing binding affinity) of myricetin to the secretases, an effective drug for the treatment of Alzheimer's Disease may be developed. Furthermore, through particular choice of docking enhancers, the metabolites of the reaction may have the additional effect of serving as anti-oxidants to repair free radical damage to brain tissue.

Myricetin is effective because of its enzyme inhibiting or promoting activity. A medicinal enzyme inhibitor is often judged by its specificity and its potency. A high specificity and potency substrate will ensure that an enzyme inhibitor will have few side effects and low toxicity. Enzyme inhibitors also occur naturally, and are involved in regulation of metabolism. This process also may be useful to control enzymes that can be damaging in cells such as the control of glucose absorption utilization and uptake in diabetics.

These inhibitors work by a process called irreversible or competitive inhibition. Competitive inhibition occurs when the substrate and inhibitor cannot bind to the enzyme at the same time. This usually results from the inhibitor having an affinity for the active site of an enzyme where the substrate also binds. The substrate and the inhibitor compete for access to the enzyme's active site. Due to this, the competitive inhibitor is often similar in structure to the real substrate.

Enzyme inhibitors are found in nature and are designed and modified as a direct drug development strategy in biochemistry and pharmacology. Natural enzyme inhibitors are often enzyme inhibitors that have evolved to defend a plant or microbe against predators.

Since the bioflavanones inhibit enzymes by competitive inhibition, which is a form of reversible binding (effective but considered weak), a method has been developed to increase the effectiveness by increasing the substrate/enzyme affinity by adding additional binding techniques to the target substrate (a phenolic compound) to change the reaction from reversible to irreversible, thus increasing its effectiveness as a new drug.

Irreversible inhibitors typically covalently modify an enzyme, and inhibition cannot therefore be reversed. Irreversible inhibitors often contain reactive functional groups such as nitrogen mustards, aldehydes, haloalkanes, alkenes, butyryl, flourophenols, sulfonomides, and hydronapthalenes. These electrophilic groups react with amino acid side chains of the target enzyme to form covalent adducts, thus enhancing the binding energy and increasing its effectiveness as a drug. The residues modified are those typically with side chains containing nucleophiles such as hydroxyl or sulfohydryl groups as is the case for metabolic regulating enzymes.

The flavonoid may be modified by attaching the above mentioned electrophilic group to any of the available positions 3, 4, 5, 6, 7, 8, 2', 3', 4', 5' and 6' of the ring structures of the Formula (A-1). Preferably, the electrophilic group(s) is attached at one or more of the positions 6, 7, 8, 3', 4', 5'. More preferably, at least one electrophilic group is attached at the 4' or 7 positions. An increase in effectiveness may be achieved by the addition of more than one electrophilic to the parent compound as well.

The term "functional group" or "electrophilic group" includes a specific group of atoms arranged or attached to a natural enzyme inhibitor (substrate) to enhance its binding affinity by increasing its electronegative potential. Such suitable compounds include alkane, alkene, benzene derivative, toluene derivative, haloalkane, flouroalkane, chloroalkane, bromoalkane, iodoalkane, acyl halide, alcohol, ketone, aldehyde, carbonate, carboxylate, carboxylic acid, ether, ester, hydroxyperoxide, peroxide, amide, amines, imine, imide, azide, azo compound, cyanates, isocyanates, nitrate, nitrile, nitrite, nitro compound, nitrous compound, pyridine derivative, phosphine, phosphodiester, phosphoric acid, phosphate, sulfide, sulfone, sulfonic acid, sulfoxide, thiol, thiocyanate, disulfide, methyl, methylene, ethyl, propyl, butyl, hydroxy, or a methoxy group.

The addition of a suitable electrophilic group to a phenolic compound such as found in the bioflavonoid compound will increase the effectiveness of the phenolic compound by changing its bonding system from a reversible to an irreversible mechanism. This alteration can be used to create effective drug candidates from a naturally occurring phenolic compound that are more effective than its natural counterpart against the target enzyme.

In general, the composition of the invention will be administered in therapeutically effective amounts by any of the usual modes known in the art. A therapeutically effective amount may vary widely depending on the disease, its severity, the age and relative health of the subject being treated, the potency of the compound as well as other factors. A person of ordinary skill in the art will be able without undue experimentation, having regard to that skill and this disclosure, to determine a therapeutically effective amount of the compound for the treatment of Alzheimer's disease and other neurological diseases.

The composition may be administered in the form of a dietary supplement, a food or beverage additive or as a pharmaceutical composition. In the modified flavonoid containing composition, the composition may include one or more additives.

Wetting agents, emulsifiers and lubricants, such as sodium lauryl sulfate and magnesium stearate, as well as coloring agents, release agents, coating agents, sweetening, flavoring agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, each containing a predetermined amount of a compound of the present invention as an active ingredient.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Embodiments of inventive compositions are illustrated in the following examples. These examples are provided for illustrative purposes and are not considered limitations on the scope of inventive compositions and methods.

EXAMPLE 1

Myricetin is modified by substituting the OH group in the $R_5$ with the electrophilic group butyryl to create a drug to treat Alzheimer's disease:

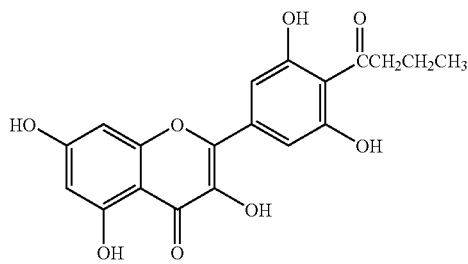

EXAMPLE 2

Myricetin is modified by substituting the OH group in the $R_4$ with the electrophilic group fluorophenol to create a drug to treat Alzheimer's disease.

EXAMPLE 3

Myricetin is modified by substituting the OH group in the $R_4$ with the electrophilic group fluorophenyl sulfoxide to create a drug to treat Alzheimer's disease.

While the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

What is claimed is:

1. A method of treating Alzheimer's disease comprising administering to a subject in need thereof a composition comprising a therapeutically effective amount of a modified flavonoid compound of the general formula:

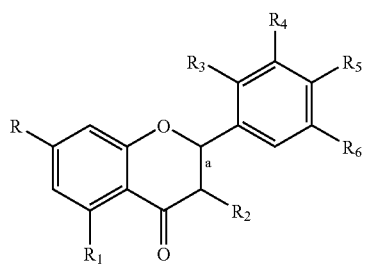

wherein R and $R_5$ are each independently hydrogen, a hydroxy group, an alkoxy group, a rutinosyl group, and a rhamnosyl group; $R_1$=OH, $R_2$=OH, $R_3$=H, $R_4$=OH and $R_6$=OH; and a is a single bond or a double bond; provided that at least one of R and $R_5$ comprises an electrophilic group chosen from aldehyde, haloalkane, alkene, butyryl, fluorophenol, sulfonamide and fluorophenyl sulfoxide.

2. The method of claim 1 wherein the electrophilic group is chosen from butyryl, sulfonamide, fluorophenol and fluorophenyl sulfoxide.

3. A method of treating Alzheimer's disease comprising administering to a subject in need thereof a composition comprising a therapeutically effective amount of a modified flavonoid compound having the structure:

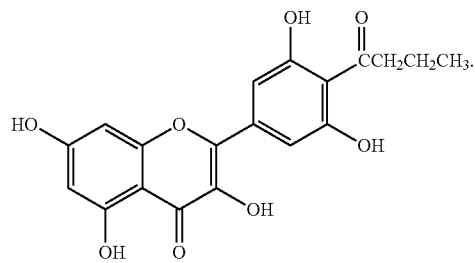

* * * * *